US009921152B2

(12) United States Patent
Krishnan et al.

(10) Patent No.: US 9,921,152 B2
(45) Date of Patent: *Mar. 20, 2018

(54) SYSTEMS AND METHODS FOR EXTENDED INFRARED SPECTROSCOPIC ELLIPSOMETRY

(71) Applicant: KLA-Tencor Corporation, Milpitas, CA (US)

(72) Inventors: Shankar Krishnan, Santa Clara, CA (US); David Y. Wang, Santa Clara, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/336,705

(22) Filed: Oct. 27, 2016

(65) Prior Publication Data

US 2017/0205342 A1 Jul. 20, 2017

Related U.S. Application Data

(60) Provisional application No. 62/279,469, filed on Jan. 15, 2016.

(51) Int. Cl.
*G01J 3/40* (2006.01)
*G01N 21/3563* (2014.01)
(Continued)

(52) U.S. Cl.
CPC ............ *G01N 21/3563* (2013.01); *G01J 3/18* (2013.01); *G01J 3/427* (2013.01); *G01N 21/211* (2013.01);
(Continued)

(58) Field of Classification Search
CPC ........ G01J 3/00; G01J 3/28; G01J 3/26; G01J 13/02; G01J 3/18
See application file for complete search history.

(56) References Cited

U.S. PATENT DOCUMENTS 5,608,526 A 3/1997 Piwonka-Corle et al.
5,859,424 A 1/1999 Norton et al.
(Continued)

OTHER PUBLICATIONS

International Search Report dated Apr. 28, 2017, for PCT Application No. PCT/US2017/012502 filed on Jan. 6, 2017 by KLA-Tencor Corporation, 4 pages.

*Primary Examiner* — Abdullahi Nur
(74) *Attorney, Agent, or Firm* — Spano Law Group; Joseph S. Spano

(57) ABSTRACT

Methods and systems for performing simultaneous spectroscopic measurements of semiconductor structures at ultraviolet, visible, and infrared wavelengths are presented herein. In another aspect, wavelength errors are reduced by orienting the direction of wavelength dispersion on the detector surface perpendicular to the projection of the plane of incidence onto the detector surface. In another aspect, a broad range of infrared wavelengths are detected by a detector that includes multiple photosensitive areas having different sensitivity characteristics. Collected light is linearly dispersed across the surface of the detector according to wavelength. Each different photosensitive area is arranged on the detector to sense a different range of incident wavelengths. In this manner, a broad range of infrared wavelengths are detected with high signal to noise ratio by a single detector. These features enable high throughput measurements of high aspect ratio structures with high throughput, precision, and accuracy.

22 Claims, 9 Drawing Sheets

(51) Int. Cl.
*G01N 21/21* (2006.01)
*G01J 3/18* (2006.01)
*G01J 3/427* (2006.01)

(52) U.S. Cl.
CPC .............. *G01J 2003/4275* (2013.01); *G01N 2021/3568* (2013.01)

(56) References Cited

U.S. PATENT DOCUMENTS

| | | | |
|---|---|---|---|
| 6,429,943 B1 | 8/2002 | Opsal et al. | |
| 6,633,831 B2 | 10/2003 | Nikoonahad et al. | |
| 6,734,967 B1 | 5/2004 | Piwonka-Corle et al. | |
| 6,816,570 B2 | 10/2004 | Janik et al. | |
| 6,895,075 B2 | 5/2005 | Yokhin et al. | |
| 6,972,852 B2 | 12/2005 | Opsal et al. | |
| 7,478,019 B2 | 1/2009 | Zangooie et al. | |
| 7,755,764 B2 | 7/2010 | Kwak et al. | |
| 7,826,071 B2 | 11/2010 | Shchegrov et al. | |
| 7,907,264 B1 | 3/2011 | Krishnan | |
| 7,929,667 B1 | 4/2011 | Zhuang et al. | |
| 7,933,026 B2 | 4/2011 | Opsal et al. | |
| 8,860,937 B1 | 10/2014 | Dziura et al. | |
| 2002/0109110 A1 | 8/2002 | Some | |
| 2003/0206292 A1 | 11/2003 | Some | |
| 2006/0066837 A1* | 3/2006 | Ortyn ............... | C12Q 1/6816 356/73 |
| 2006/0289790 A1 | 12/2006 | Raymond et al. | |
| 2010/0118300 A1 | 5/2010 | Wang | |
| 2013/0114085 A1 | 5/2013 | Wang et al. | |
| 2013/0342673 A1 | 12/2013 | Sticker et al. | |
| 2014/0111791 A1 | 4/2014 | Manassen et al. | |
| 2014/0166862 A1* | 6/2014 | Flock ............... | G01N 21/9501 250/208.2 |
| 2014/0172394 A1 | 6/2014 | Kuznetsov et al. | |
| 2014/0222380 A1 | 8/2014 | Kuznetsov et al. | |
| 2014/0297211 A1 | 10/2014 | Pandev et al. | |
| 2014/0316730 A1 | 10/2014 | Shchegrov et al. | |
| 2015/0042984 A1 | 2/2015 | Pandev et al. | |
| 2015/0046118 A1 | 2/2015 | Pandev et al. | |

\* cited by examiner

SYSTEMS AND METHODS FOR EXTENDED INFRARED SPECTROSCOPIC ELLIPSOMETRY

CROSS REFERENCE TO RELATED APPLICATION

The present application for patent claims priority under 35 U.S.C. § 119 from U.S. provisional patent application Ser. No. 62/279,469, entitled "Apparatus and Methods of Extended Infrared Ellipsometry," filed Jan. 15, 2016, the subject matter of which is incorporated herein by reference in its entirety.

TECHNICAL FIELD

The described embodiments relate to metrology systems and methods, and more particularly to methods and systems for improved measurement of three dimensional semiconductor structures.

BACKGROUND INFORMATION

Semiconductor devices such as logic and memory devices are typically fabricated by a sequence of processing steps applied to a specimen. The various features and multiple structural levels of the semiconductor devices are formed by these processing steps. For example, lithography among others is one semiconductor fabrication process that involves generating a pattern on a semiconductor wafer. Additional examples of semiconductor fabrication processes include, but are not limited to, chemical-mechanical polishing, etch, deposition, and ion implantation. Multiple semiconductor devices may be fabricated on a single semiconductor wafer and then separated into individual semiconductor devices.

Metrology processes are used at various steps during a semiconductor manufacturing process to detect defects on wafers to promote higher yield. Optical metrology techniques offer the potential for high throughput without the risk of sample destruction. A number of optical metrology based techniques including scatterometry and reflectometry implementations and associated analysis algorithms are commonly used to characterize critical dimensions, film thicknesses, composition, overlay and other parameters of nanoscale structures.

Flash memory architectures are transitioning from two dimensional floating-gate architectures to fully three dimensional geometries. In some examples, film stacks and etched structures are very deep (e.g., up to six micrometers in depth). Such high aspect ratio structures create challenges for film and CD measurements. The ability to measure the critical dimensions that define the shapes of holes and trenches of these structures is critical to achieve desired performance levels and device yield.

Many optical techniques suffer from low signal-to-noise ratios (SNRs), as only a small fraction of the illumination light is able to reach the bottom of high aspect ratio features, and reflect upwards to the detector. Thus, many available high-throughput metrology techniques are unable to reliably perform CD and film measurements of high aspect ratio structures. Critical dimension, small angle X-ray scatterometry (CD-SAXS), normal incidence reflectometry, and scatterometry are being explored as measurement solutions for high aspect ratio structures, but development is still ongoing.

Cross-sectional scanning electron microscopy (SEM) is a low throughput, destructive technique that is not suitable for inline metrology. Atomic force microscopy (AFM) is limited in its ability to measure high aspect ratio structures and has relatively low throughput. CD-SAXS has not yet been demonstrated to achieve high throughput capabilities required by the semiconductor industry. Model based infrared reflectometry (MBIR) has been used for metrology of high aspect ratio DRAM structures, but the technique lacks the resolution provided by shorter wavelengths and the measurement spot sizes are too large for semiconductor metrology. See "Measuring deep-trench structures with model-based IR," by Gostein et al., Solid State Technology, vol. 49, no. 3, Mar. 1, 2006, which is incorporated by reference as if fully set forth herein.

Optical CD metrology currently lacks the ability to measure the detailed profile of structures with micron scale depths and lateral dimensions in a relatively small spot (e.g., less than 50 microns, or even more preferably, less than 30 microns) at high throughput. U.S. Pat. No. 8,860,937, which is incorporated by reference as if fully set forth herein, describes infrared spectroscopic ellipsometry techniques that are suitable for characterization of high aspect ratio structures. However, the described techniques suffer from long measurement times for measurements spanning the ultraviolet and infrared wavelengths, wavelength stability limitations, and limited range of infrared wavelengths during operation.

In summary, ongoing reductions in feature size and increasing depths of structural features impose difficult requirements on optical metrology systems. Optical metrology systems must meet high precision and accuracy requirements for increasingly complex targets at high throughput to remain cost effective. In this context, speed of broadband illumination and data collection, focusing errors, and range of infrared wavelengths have emerged as critical, performance limiting issue in the design of optical metrology systems suitable for high aspect ratio structures. Thus, improved metrology systems and methods to overcome these limitations are desired.

SUMMARY

Methods and systems for performing simultaneous spectroscopic measurements of semiconductor structures at ultraviolet, visible, and infrared wavelengths are presented herein. Spectra including ultraviolet, visible, and infrared wavelengths are measured at high throughput with the same alignment conditions. In this manner, machine errors, such as wavelength errors, are uniformly corrected across all measured wavelengths. By simultaneously measuring a target with infrared, visible, and ultraviolet light in a single system, precise characterization of complex three dimensional structures is enabled. In general, relatively long wavelengths penetrate deep into a structure and provide suppression of high diffraction orders when measuring structures with relatively large pitch. Relatively short wavelengths provide precise dimensional information about structures accessible to relatively short wavelengths (i.e., top level layers) as well as relatively small CD and roughness features. In some examples, longer wavelengths enable measurement of dimensional characteristics of targets with relatively rough surfaces or interfaces due to lower sensitivity of longer wavelengths to roughness.

In another aspect, a fine focus sensor (FFS) is integrated into the detection subsystem to provide measurement input for focus error correction during measurement.

In another aspect, a broadband spectroscopic metrology system is configured such that the measurement spot is imaged onto the detector such that the direction aligned with the plane of incidence on the wafer surface is oriented perpendicular to the direction of wavelength dispersion on the detector surface. In this arrangement, the sensitivity of the metrology system to focus errors is greatly reduced. With reduced sensitivity to focus errors, precise measurements are obtained with shorter MAM times, and thus, higher throughput.

In another aspect, the metrology systems described herein employ a multi-zone infrared detector that combines different sensitivity bands at different locations on a single detector package. The detector is configured to deliver a continuous spectrum of data at different sensitivities, depending on location of incidence. Collected light is linearly dispersed across the surface of the detector according to wavelength. Each different photosensitive area is arranged on the detector to sense a different range of incident wavelengths. In this manner, a broad range of infrared wavelengths are detected with high signal to noise ratio by a single detector.

In a further aspect, the dimension of the illumination field projected on the wafer plane in the direction perpendicular to the plane of incidence is adjusted to optimize the resulting measurement accuracy and speed based on the nature of target under measurement.

The foregoing is a summary and thus contains, by necessity, simplifications, generalizations and omissions of detail; consequently, those skilled in the art will appreciate that the summary is illustrative only and is not limiting in any way. Other aspects, inventive features, and advantages of the devices and/or processes described herein will become apparent in the non-limiting detailed description set forth herein.

DETAILED DESCRIPTION

Figure 1:
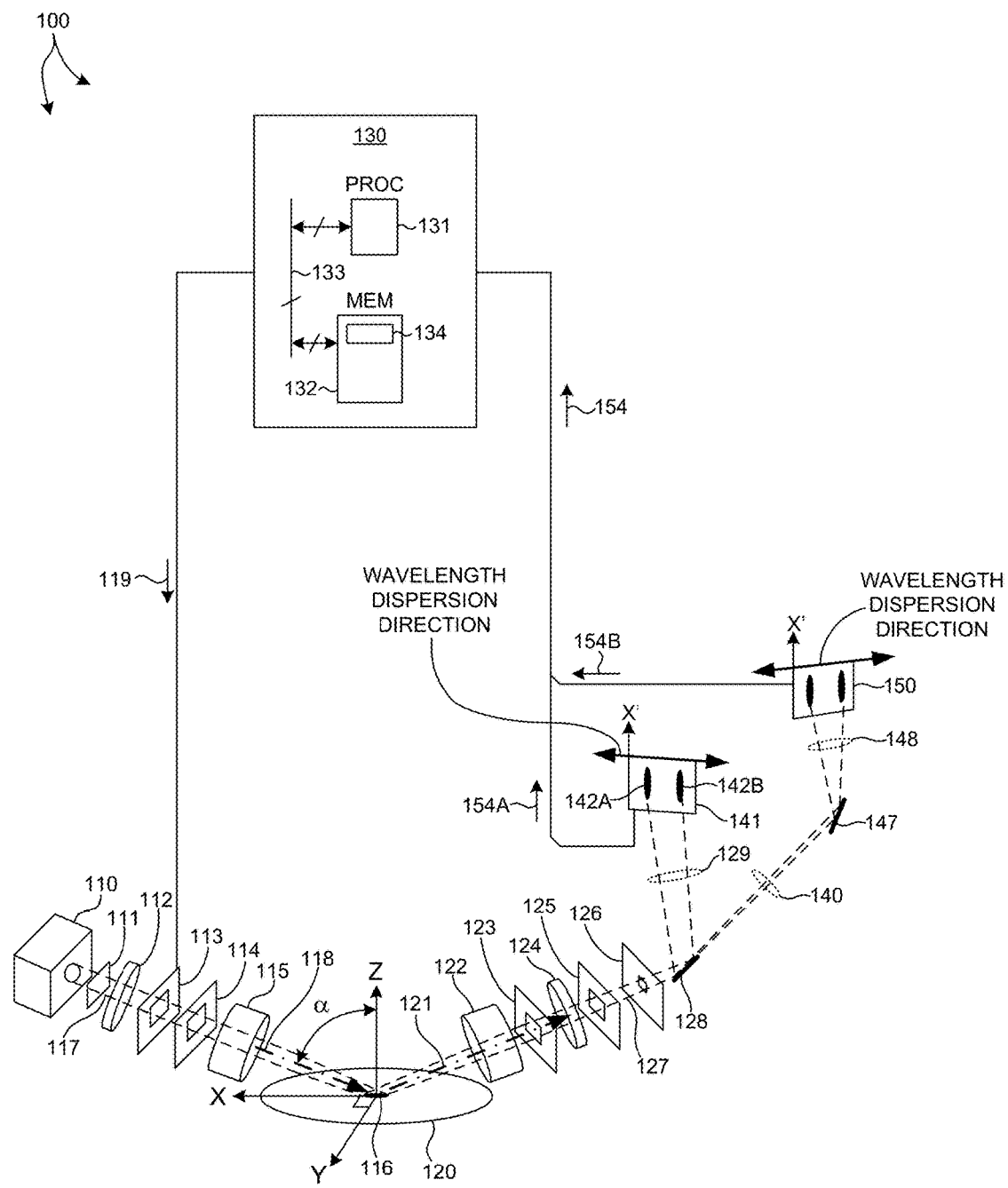
FIG. 1 depicts an exemplary, metrology system 100 for performing simultaneous spectroscopic measurements of one or more structures at ultraviolet, visible, and infrared wavelengths in one embodiment.

Reference will now be made in detail to background examples and some embodiments of the invention, examples of which are illustrated in the accompanying drawings.

Methods and systems for performing simultaneous spectroscopic measurements of semiconductor structures at ultraviolet, visible, and infrared wavelengths are presented herein. Spectra including ultraviolet, visible, and infrared wavelengths are measured at high throughput with the same alignment conditions. In this manner, machine errors, such as wavelength errors, are uniformly corrected across all measured wavelengths. In another aspect, wavelength errors are reduced by orienting the direction of wavelength dispersion on the detector surface perpendicular to the projection of the plane of incidence onto the detector surface. In another aspect, a broad range of infrared wavelengths are detected by a detector that includes multiple photosensitive areas having different sensitivity characteristics. Collected light is linearly dispersed across the surface of the detector according to wavelength. Each different photosensitive area is arranged on the detector to sense a different range of incident wavelengths. In this manner, a broad range of infrared wavelengths are detected with high signal to noise ratio by a single detector. These features, individually, or in combination, enable high throughput measurements of high aspect ratio structures (e.g., structures having depths of one micrometer or more) with high throughput, precision, and accuracy.

By simultaneously measuring a target with infrared, visible, and ultraviolet light in a single system, precise characterization of complex three dimensional structures is enabled. In general, relatively long wavelengths penetrate deep into a structure and provide suppression of high diffraction orders when measuring structures with relatively large pitch. Relatively short wavelengths provide precise dimensional information about structures accessible to relatively short wavelengths (i.e., top level layers) as well as relatively small CD and roughness features. In some examples, longer wavelengths enable measurement of dimensional characteristics of targets with relatively rough surfaces or interfaces due to lower sensitivity of longer wavelengths to roughness.

In some embodiments, the methods and systems for spectroscopic metrology of semiconductor devices described herein are applied to the measurement of high aspect ratio (HAR), large lateral dimension structures, or both. These embodiments enable optical critical dimension (CD), film, and composition metrology for semiconductor devices with HAR structures (e.g., NAND, VNAND, TCAT, DRAM, etc.) and, more generally, for complex devices that suffer from low light penetration into the structure(s) being measured. HAR structures often include hard mask layers to facilitate etch processes for HARs. As described herein, the term "HAR structure" refers to any structure characterized by an aspect ratio that exceeds 10:1 and may be as high as 100:1, or higher.

FIG. 1 depicts an exemplary, metrology system 100 for performing simultaneous spectroscopic measurements of one or more structures at ultraviolet, visible, and infrared wavelengths. In some examples, the one or more structures include at least one HAR structure or at least one large lateral dimension structure. As depicted in FIG. 1, metrology system 100 is configured as a broadband spectroscopic ellipsometer. However, in general, metrology system 100 may be configured as a spectroscopic reflectometer, scatterometer, ellipsometer, or any combination thereof.

Metrology system 100 includes an illumination source 110 that generates a beam of illumination light 117 incidence on a wafer 120. Illumination source 110 is a broadband illumination source that emits illumination light in the ultraviolet, visible, and infrared spectra. In one embodiment, illumination source 110 is a laser sustained plasma (LSP) light source (a.k.a., laser driven plasma source). The pump laser of the LSP light source may be continuous wave or pulsed. A laser-driven plasma source can produce significantly more photons than a Xenon lamp across the entire wavelength range from 150 nanometers to 2000 nanometers. Illumination source 110 can be a single light source or a combination of a plurality of broadband or discrete wavelength light sources. The light generated by illumination source 110 includes a continuous spectrum or parts of a continuous spectrum, from ultraviolet to infrared (e.g., vacuum ultraviolet to mid infrared). In general, illumination light source 110 may include a super continuum laser source, an infrared helium-neon laser source, an arc lamp, or any other suitable light source.

In a further aspect, the amount of illumination light is broadband illumination light that includes a range of wavelengths spanning at least 500 nanometers. In one example, the broadband illumination light includes wavelengths below 250 nanometers and wavelengths above 750 nanometers. In general, the broadband illumination light includes wavelengths between 120 nanometers and 3,000 nanometers. In some embodiments, broadband illumination light including wavelengths beyond 3,000 nanometers may be employed.

As depicted in FIG. 1, metrology system 100 includes an illumination subsystem configured to direct illumination light 117 to one or more structures formed on the wafer 120. The illumination subsystem is shown to include light source 110, one or more optical filters 111, polarizing component 112, field stop 113, aperture stop 114, and illumination optics 115. The one or more optical filters 111 are used to control light level, spectral output, or both, from the illumination subsystem. In some examples, one or more multi-zone filters are employed as optical filters 111. Polarizing component 112 generates the desired polarization state exiting the illumination subsystem. In some embodiments, the polarizing component is a polarizer, a compensator, or both, and may include any suitable commercially available polarizing component. The polarizing component can be fixed, rotatable to different fixed positions, or continuously rotating. Although the illumination subsystem depicted in FIG. 1 includes one polarizing component, the illumination subsystem may include more than one polarizing component. Field stop 113 controls the field of view (FOV) of the illumination subsystem and may include any suitable commercially available field stop. Aperture stop 114 controls the numerical aperture (NA) of the illumination subsystem and may include any suitable commercially available aperture stop. Light from illumination source 110 is directed through illumination optics 115 to be focused on one or more structures (not shown in FIG. 1) on wafer 120. The illumination subsystem may include any type and arrangement of optical filter(s) 111, polarizing component 112, field stop 113, aperture stop 114, and illumination optics 115 known in the art of spectroscopic ellipsometry, reflectometry, and scatterometry.

As depicted, in FIG. 1, the beam of illumination light 117 passes through optical filter(s) 111, polarizing component 112, field stop 113, aperture stop 114, and illumination optics 115 as the beam propagates from the illumination source 110 to wafer 120. Beam 117 illuminates a portion of wafer 120 over a measurement spot 116.

In some examples, the beam size of the amount of illumination light 117 projected onto the surface of wafer 120 is smaller than a size of a measurement target that is measured on the surface of the specimen. Exemplary beam shaping techniques are described in detail in U.S. Patent Application Publication No. 2013/0114085 by Wang et al., the contents of which are incorporated herein by reference in their entirety.

Metrology system 100 also includes a collection optics subsystem configured to collect light generated by the interaction between the one or more structures and the incident illumination beam 117. A beam of collected light 127 is collected from measurement spot 116 by collection optics 122. Collected light 127 passes through collection aperture stop 123, polarizing element 124, and field stop 125 of the collection optics subsystem.

Collection optics 122 includes any suitable optical elements to collect light from the one or more structures formed on wafer 120. Collection aperture stop 123 controls the NA of the collection optics subsystem. Polarizing element 124 analyzes the desired polarization state. The polarizing element 124 is a polarizer or a compensator. The polarizing element 124 can be fixed, rotatable to different fixed positions, or continuously rotating. Although the collection subsystem depicted in FIG. 1 includes one polarizing element, the collection subsystem may include more than one polarizing element. Collection field stop 125 controls the FOV of the collection subsystem. The collection subsystem takes light from wafer 120 and directs the light through collection optics 122, and polarizing element 124 to be focused on collection field stop 125. In some embodiments, collection field stop 125 is used as a spectrometer slit for the spectrometers of the detection subsystem. However, collection field stop 125 may be located at or near a spectrometer slit 126 of the spectrometers of the detection subsystem.

The collection subsystem may include any type and arrangement of collection optics 122, aperture stop 123, polarizing element 124, and field stop 125 known in the art of spectroscopic ellipsometry, reflectometry, and scatterometry.

In the embodiment depicted in FIG. 1, the collection optics subsystem directs light to more than one spectrometer of the detection subsystem. The detection subsystem generates output responsive to light collected from the one or more structures illuminated by the illumination subsystem.

In one aspect, the detector subsystem includes two or more detectors each configured to detect collected light over different wavelength ranges, including infrared, simultaneously.

In the embodiment depicted in FIG. 1, collected light 127 passes through spectrometer slit 126 and is incident on diffractive element 128. Diffractive element 128 is configured to diffract a subset of wavelengths of the incident light into the +/−1 diffraction order and diffract a different subset of wavelengths of the incident light into the zero diffraction order. As depicted in FIG. 1, portion 129 of the incident light including the ultraviolet spectrum is dispersed at the +/−1 diffraction order toward detector 141 by diffractive element 128. In addition, diffractive element 128 is configured to reflect portion 140 of the incident light including infrared wavelengths at the zero diffraction order toward grating 147. Light 140 is incident on diffractive element 147 and diffractive element 147 disperses portion 148 of the incident light 140 including infrared wavelengths at the +/−1 diffraction order toward detector 150.

In the embodiment depicted in FIG. 1, diffractive element 128 is a reflective grating element. However, in general, diffractive element 128 may be configured to subdivide the incident light into different wavelength bands, propagate the different wavelength bands in different directions, and disperse the light of one of the wavelength bands onto a detector in any suitable manner. In one example, diffractive element 128 is configured as a transmissive grating. In some other examples, diffractive element 128 includes a beam-splitting element to subdivide the beam into different wavelength bands and a reflective or transmissive grating structure to disperse one of the wavelength bands onto detector 141.

Reflective grating 128 is employed because it exhibits high diffraction efficiency into the +−1 orders in the ultraviolet spectral region and high diffraction efficiency into the zeroth diffraction order for the infrared spectral region. By employing a reflective grating, losses inherent to beam splitting elements (such as a dichroic beam splitting element) are avoided.

The diffractive elements 128 and 147 linearly disperse first order diffracted light according to wavelength along one dimension of each respective two dimensional detector (i.e., the wavelength dispersion direction noted in FIG. 1 for each respective detector). For purposes of illustration, light detected at two different wavelengths is illustrated on the surface of detector 141. Diffractive element 128 causes a spatial separation between the two different wavelengths of light projected onto the surface of detector 141. In this manner, light collected from measurement spot 116 having a particular wavelength is projected onto detector 141 over spot 142A and light collected from measurement spot 116 having another, different wavelength is projected onto detector 141 over spot 142B.

In one example, detector 141 is a charge coupled device (CCD) sensitive to ultraviolet and visible light (e.g., light having wavelengths between 190 nanometers and 860 nanometers). In one example, detector 150 is a photo detector array (PDA) sensitive to infrared light (e.g., light having wavelengths between 950 nanometers and 2500 nanometers). However, in general, other two dimensional detector technologies may be contemplated (e.g., a position sensitive detector (PSD), an infrared detector, a photovoltaic detector, etc.). Each detector converts the incident light into electrical signals indicative of the spectral intensity of the incident light. For example, UV detector 141 generates output signals 154A indicative of incident light 129 and IR detector 150 generates output signals 154B indicative of incident light 148.

As depicted in FIG. 1, the detection subsystem is arranged such that the collected light propagates to all detectors of metrology system 100, simultaneously. Metrology system 100 also includes computing system 130 configured to receive detected signals 154, including both UV and IR signals, and determines an estimate of a value of a parameter of interest of the measured structure(s) based on both the UV and IR signals. By simultaneously collecting UV and IR spectra measurement times are reduced and all spectra are measured with the same alignment conditions. This allows wavelength errors to be corrected more easily because a common correction can be applied to all spectral data sets.

In a further aspect, a fine focus sensor (FFS) is integrated into the detection subsystem to provide measurement input for focus error correction during measurement.

Figure 2:
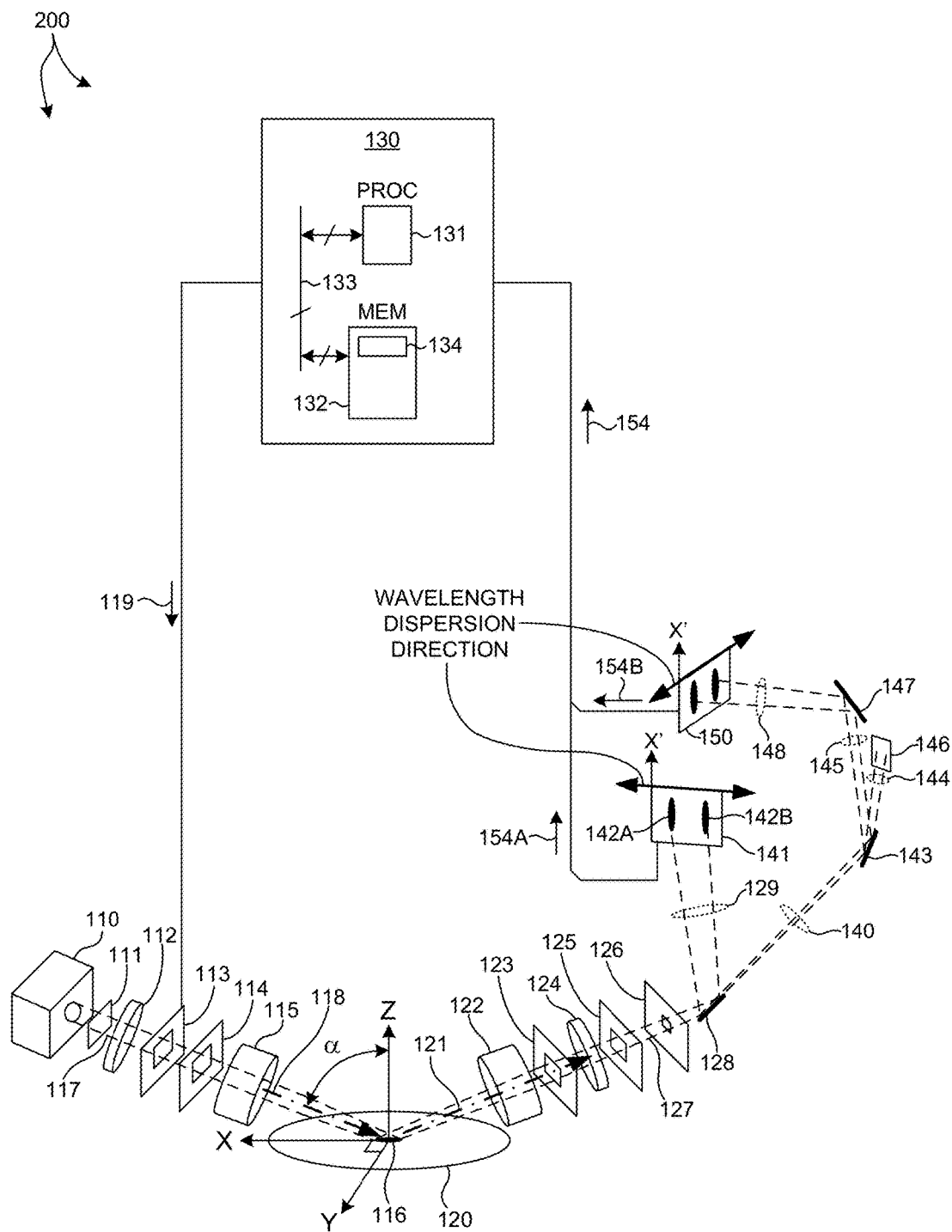
FIG. 2 depicts an exemplary, metrology system 100 for performing simultaneous spectroscopic measurements of one or more structures at ultraviolet, visible, and infrared wavelengths in another embodiment.

FIG. 2 depicts another embodiment 200 of a metrology system including a FFS 146. Elements shown in FIG. 2 that are similarly configured as metrology system 100 depicted in FIG. 1 have been indicated using the same reference numerals. As depicted in FIG. 2, the 0th diffracted order light 140 diffracted from diffractive element 128 is incident on beam splitting element 143. Beam splitting element 143 can be transmissive or reflective. Beam splitting element 143 directs the portion of light 145 in the IR range toward IR grating 147 and the portion of light 144 below the IR range (i.e., UV to visible range) toward FFS 146. In this manner, the UV to visible light diffracted from diffractive element 128 at the zeroth order is detected by FFS 146. In some embodiments, FFS 146 is a photo diode array and beam splitting element 143 is a dichroic beamsplitter capable of high IR efficiency in reflection and high UV efficiency in transmission. In some other embodiments, beams splitting element 143 is a neutral density filter, partially reflecting mirror, uncoated substrate, or any other suitable optical element that divides the beam into two or more beams of lesser intensity for the individual channels.

Output generated by FFS 146 (not shown) is communicated to computing system 130. Computing system 130 determines changes in focus position (z-position) of wafer 120 based on the output of FFS 146. Any desired changes in focus position of wafer 120 are communicated to a wafer positioning system (not shown) that adjusts the z-position of wafer 120, accordingly.

Figure 3:
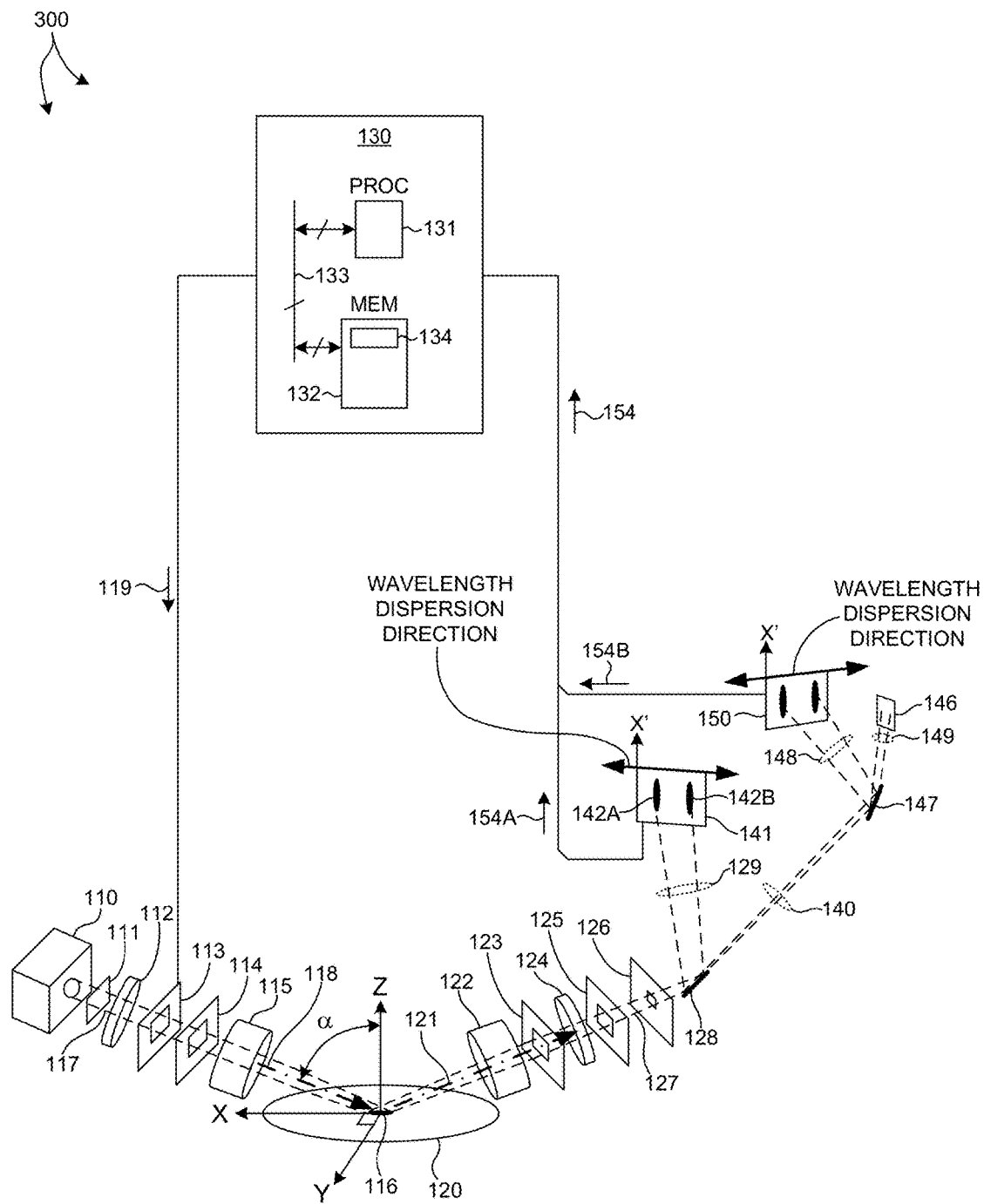
FIG. 3 depicts an exemplary, metrology system 100 for performing simultaneous spectroscopic measurements of one or more structures at ultraviolet, visible, and infrared wavelengths in yet another embodiment.

FIG. 3 depicts another embodiment 300 of a metrology system including a FFS 146. Elements shown in FIG. 3 that are similarly configured as metrology system 100 depicted in FIG. 1 have been indicated using the same reference numerals. As depicted in FIG. 3, the 0th diffracted order light 149 diffracted from the diffractive element 147 is incident on FFS 146, while first order diffracted light 148 is incident on IR detector 150.

Output generated by FFS 146 (not shown) is communicated to computing system 130. Computing system 130 determines changes in focus position (z-position) of wafer 120 based on the output of FFS 146. Any desired changes in focus position of wafer 120 are communicated to a wafer positioning system (not shown) that adjusts the z-position of wafer 120, accordingly.

In another further aspect, a metrology system includes two or more detectors configured to simultaneously detect light in different ranges of the IR spectrum.

Figure 4:
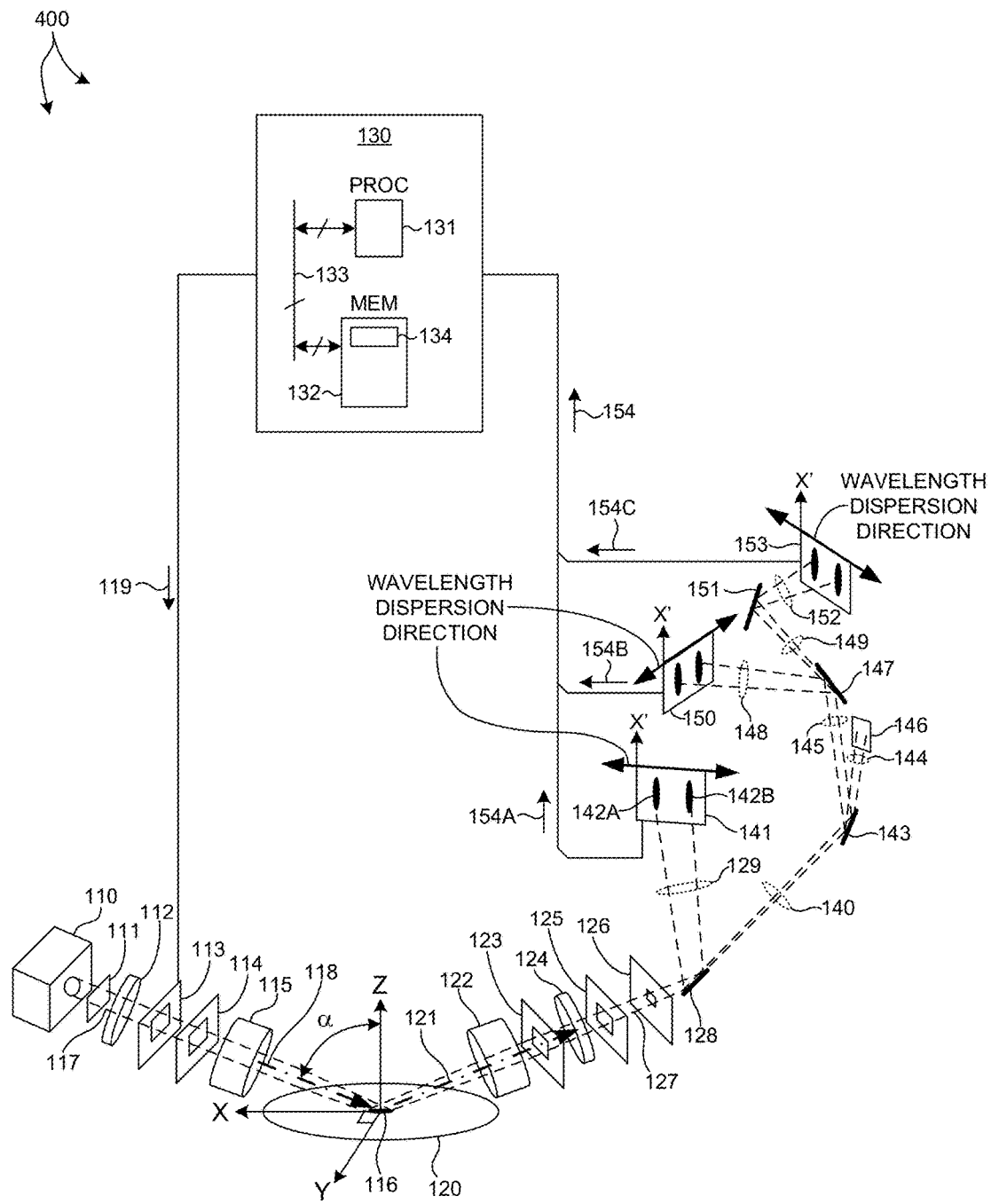
FIG. 4 depicts an exemplary, metrology system 100 for performing simultaneous spectroscopic measurements of one or more structures at ultraviolet, visible, and infrared wavelengths in yet another embodiment.

FIG. 4 depicts another embodiment 400 of a metrology system including multiple, cascaded IR detectors. Elements shown in FIG. 4 that are similarly configured as metrology system 100 depicted in FIG. 1 have been indicated using the same reference numerals. As depicted in FIG. 4, light 145 is incident to IR grating 147. IR grating 147 is configured to diffract a portion 148 of the incident light 145 at a first order. The first order diffracted light 148 includes a subset of the range of IR wavelengths of incident light 145. Furthermore, IR grating 147 is configured to diffract a portion 149 of the incident light 145 at the zeroth order. The zeroth order diffracted light 149 includes IR wavelengths outside the range of IR wavelengths that make up first order diffracted light 148. The zeroth order diffracted light 149 propagates to IR grating 151, which diffracts the incident light at the first order toward IR detector 153. In the embodiment depicted in FIG. 4, the first order diffracted light 152 includes all of the IR wavelengths of incident light 149. However, in some other embodiments, IR grating 151 is configured to diffract only a portion of the incident light at first order, and the remaining zeroth order light is directed toward yet another IR grating. In this manner, any number of IR detectors may be cascaded together to detect distinct ranges of IR wavelengths of collected light 127.

The embodiments described with reference to FIGS. 1-4 are provided by way of non-limiting example, as many other configurations for simultaneously detecting UV, visible, and IR wavelengths may be contemplated. In one example, a metrology system may be configured to disperse IR wavelengths of collected light 127 at the first diffraction orders and diffract UV wavelengths of collected light 127 at the zero order toward a UV grating and detector. In some examples, beam splitting elements may be employed to sub-divide the full spectrum of collected light into two or more sub-spectrums. However, it may be advantageous to employ diffractive elements as described herein to avoid the losses inherent to beam splitting elements such as dichroic beam splitters, neutral density filters, partially reflecting mirrors, or uncoated substrates.

As depicted in FIG. 1, the beam of illumination light 117 is provided to the surface of wafer 120 at an oblique angle. In general, illumination light may be provided to the surface of wafer 120 at any oblique angle or number of oblique angles. In some embodiments, an amount of illumination light is provided to the surface at normal incidence (i.e., aligned with the surface normal) in addition to oblique illumination.

As depicted in FIG. 1, the Z-axis is oriented normal to the surface of wafer 120. The X and Y axes are coplanar with the surface of wafer 120, and thus perpendicular to the Z-axis. The chief ray 118 of the beam of illumination light 117 and the chief ray 121 of the beam of collected light 127 define a plane of incidence. The X-axis is aligned with the plane of incidence and the Y-axis is orthogonal to the plane of incidence. In this manner, the plane of incidence lies in the XZ plane. The beam of illumination light 117 is incident on the surface of wafer 120 at an angle of incidence, $\alpha$, with respect to the Z-axis and lies within the plane of incidence. The geometric projection of a beam of illumination light onto the surface of a specimen at an oblique angle results in an elongation of the illumination beam cross-section in the direction aligned with the plane of incidence. By way of non-limiting example, a circular beam of illumination light projected on the wafer surface results in an illumination area that is elliptical in shape. Thus, in general, oblique illumination of a surface results in a projected illumination area that is elongated relative to the illumination cross section and the direction of elongation is aligned with the plane of incidence. Moreover, the magnitude of the elongation increases as the angle of incidence increases. More specifically, the beam shape is inversely proportional to the cosine of the angle of incidence in the direction of the plane of incidence. In the absence of diffraction and aberration effects, the projected illumination light remains undistorted in the direction perpendicular to the plane of illumination (e.g., Y-direction).

Figure 5A:
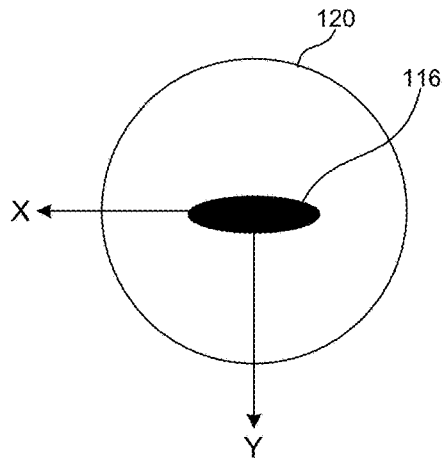
FIG. 5A depicts a top-view of wafer 120 including a depiction of measurement spot 116 illuminated by the beam of illumination light 117 of FIG. 1.

FIG. 5A depicts a top-view of wafer 120 including a depiction of measurement spot 116 illuminated by the beam of illumination light 117 of FIG. 1. In the embodiment depicted in FIG. 1, the cross-section of the beam of illumination light 117 is circular in shape (e.g., at illumination field stop 113). For a circular beam of illumination light, the measurement spot 116 projected on the surface of wafer 120 is elliptical in shape as depicted in FIG. 5A.

As depicted in FIG. 1, measurement spot 116 is projected onto the surface of detectors 141 and 150 in a wavelength dispersive manner. In another aspect, the spectrometer components of the metrology systems described herein are configured such that the plane of dispersion of light onto each of the detectors is oriented perpendicular to the projection of the plane of incidence on each respective detector. In this manner, the measurement spot 116 is imaged onto each detector such that the direction aligned with the plane of incidence on the wafer surface is oriented perpendicular to the direction of wavelength dispersion on the detector surface. In this arrangement, the sensitivity of the metrology system to focus errors is greatly reduced. With reduced sensitivity to focus errors, precise measurements are obtained with shorter MAM times, and thus, higher throughput. A significant advantage of this architecture is the ability to measure thick and multilayer film stacks without incurring wavelength errors.

Figure 5B:
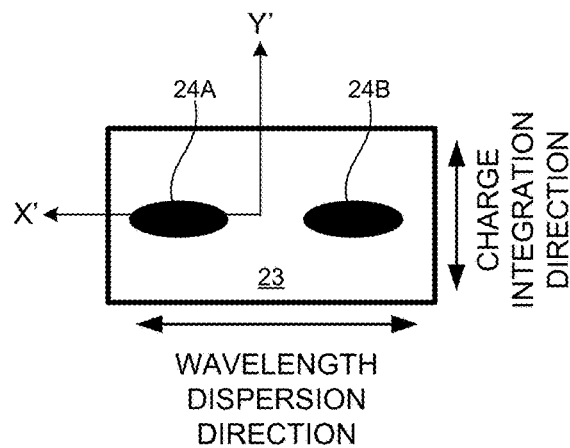
FIG. 5B depicts a normal view of the surface of a detector 23 in a metrology system in a traditional configuration.

Traditionally, metrology systems are configured such that the projection of the elongated direction of a measurement spot is aligned with the direction of wavelength dispersion on the surface of the detector. FIG. 5B is representative of the traditional configuration. As depicted in FIG. 5B, the projection of the elongated direction of a measurement spot 116 (i.e., the X-axis at wafer and X' axis at detector) onto detector 23 is aligned with the direction of wavelength dispersion on the surface of the detector 23. By way of example, the elongated direction of spots 24A and 24B is aligned with the wavelength dispersion direction. The wavelength dependent images (e.g., spots 24A and 24B) on the surface of detector 23 are integrated in the direction perpendicular to the wavelength dispersion direction to obtain a spectrum, i.e., intensity as a function of wavelength along the wavelength dispersion axis. For a CCD detector, charge is integrated in the direction perpendicular to wavelength dispersion to arrive at the spectrum.

When the measurement spot is imaged onto the detector such that the direction aligned with the plane of incidence on the wafer surface is aligned with the direction of wavelength dispersion on the detector surface, the resulting point spread function (PSF) is strongly wavelength dependent. The resulting PSF is highly peaked because the image intensity varies greatly in the elongated direction for a given wavelength. To properly capture the highly peaked PSD the spectrometer must acquire spectral data at high resolution. This increases measurement time and reduces throughput.

In another example, the resulting PSF for a particular wavelength depends on the angle of incidence when the elongated image, and corresponding elongated intensity distribution, is aligned with the direction of spectral dispersion. The resulting PSF broadens or narrows depending on the angle of incidence.

Figure 6:
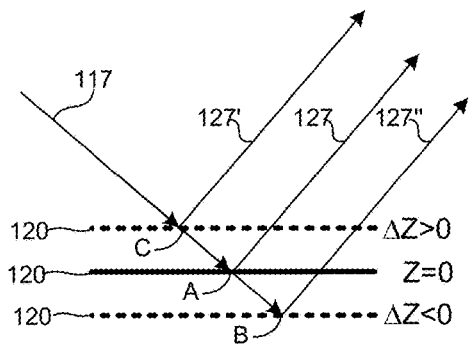
FIG. 6 illustrates a wafer 120 subject to focus position errors.
Figure 7:
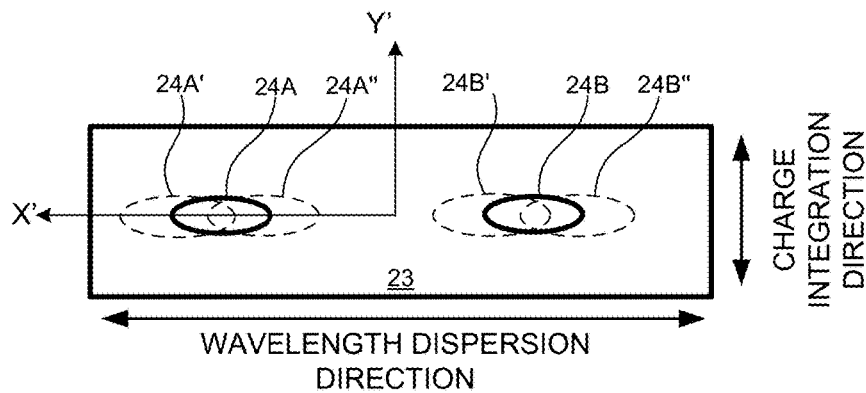
FIG. 7 illustrates a beam of collected light that is wavelength dispersed and imaged onto the surface of a detector 23 in a traditional manner.

In another example, the resulting PSF is highly sensitive to focus errors. As the measurement target on wafer moves in and out of focus, the detected image of the measurement spot on the wafer changes size and shifts location. In addition, the location of the measurement spot on the wafer shifts. As illustrated in FIG. 6, when wafer 120 is in focus, the beam of illumination light 117 illuminates the wafer at location A. If the beam of collected light 127 is wavelength dispersed and imaged onto detector 23 in the traditional manner, it appears at spots 24A and 24B as illustrated in FIG. 7. As the wafer 120 is moved upward in the z-direction and is defocused by an amount, $\Delta Z$, that is greater than zero, the beam of illumination light 117 illuminates the wafer at location C. If the beam of collected light 127' is wavelength dispersed and imaged onto detector 23 in the traditional manner, it appears at spots 24A' and 24B'. The resulting images are larger as the wafer is moved away from the focal plane of the optical system and the center position of the images shifts in the direction aligned with the wavelength dispersion direction. This shift in the wavelength dispersion direction results in spectral measurement errors as the wavelength to pixel mapping changes. As the wafer 120 is moved downward in the z-direction and is defocused by an amount, $\Delta Z$, that is less than zero, the beam of illumination light 117 illuminates the wafer at location B. If the beam of collected light 127" is wavelength dispersed and imaged onto detector 23 in the traditional manner it appears at spots 24A" and 24B". Again, the resulting images are larger as the wafer is moved away from the focal plane of the optical system and the center position of the images shifts in the direction aligned with the wavelength dispersion direction.

In this scenario, the measurement spot movement on wafer 120 due to focus error, i.e., $\Delta Z \neq 0$, results in image movement along the spectrometer dispersive axis as a function of wavelength. Since wavelength calibration is performed in the focal plane, i.e., $Z=0$, any image movement in the spectrometer dispersive direction induced by focus errors makes the measured spectrum very sensitive to deviations from the wavelength calibration.

However, by projecting the plane of incidence onto the detector perpendicular to the direction of wavelength dispersion as described herein, the dispersion plane is decoupled from the plane of incidence, and consequently focus errors do not impact the spectrum location on the detector.

As depicted in FIG. 1, measurement spot 116 is projected onto the surfaces of detector 141 and detector 150 in a wavelength dispersive manner. Metrology system 100 is configured such that the projection of the elongated direction of measurement spot 116 is oriented perpendicular to the direction of wavelength dispersion on the surface of detectors 141 and 150. The X'-axis depicted in FIG. 1 is representative of the projection of the elongated direction of measurement spot 116 (i.e., the X-axis) onto detectors 141 and 150. As depicted in FIG. 1, the X'-axis is oriented perpendicular to the direction of wavelength dispersion on the surface of detectors 141 and 150.

In some examples, a twenty times reduction in sensitivity to focus position is achieved by imaging the measurement spot onto the detector such that the direction aligned with the plane of incidence on the wafer surface is oriented perpendicular to the direction of wavelength dispersion on the detector surface. This reduction in focus error sensitivity enables reduced focus accuracy and repeatability requirements, faster focus times, and reduced sensitivity to wavelength errors without compromising measurement accuracy. These benefits are particularly evident in large numerical aperture optical metrology systems.

Figure 8:
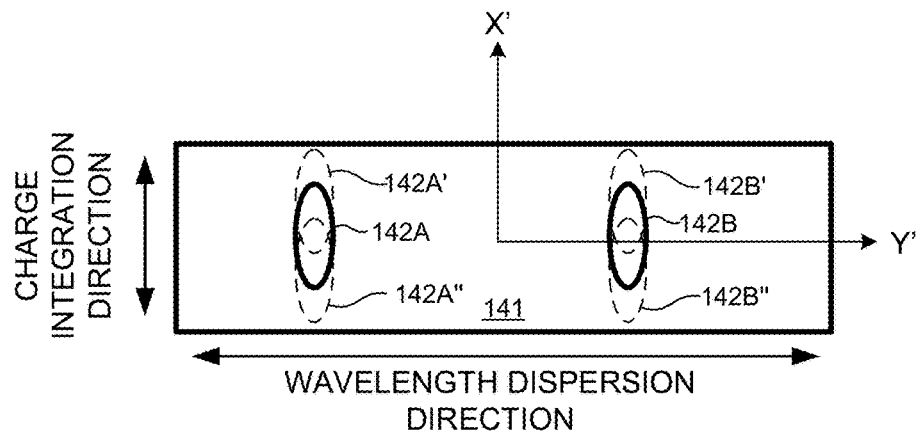
FIG. 8 depicts a normal view of the surface of detector 141 depicted in FIG. 1.

FIG. 8 depicts a normal view of the surface of detector 141. As depicted in FIG. 8, the projection of the elongated direction of measurement spot 116 (i.e., X'-axis) is oriented perpendicular to the direction of wavelength dispersion across the surface of detector 141. By way of example, the elongated direction of spots 142A and 142B is oriented perpendicular to the wavelength dispersion direction. The wavelength dependent images (e.g., spots 142A and 142B) on the surface of detector 141 are integrated in the direction perpendicular to the wavelength dispersion direction to obtain a spectrum, i.e., intensity as a function of wavelength along the wavelength dispersion axis. For a CCD detector, charge is integrated in the direction perpendicular to wavelength dispersion to arrive at the spectrum.

The images projected onto the surface of the detector (e.g., CCD 141) are integrated in the direction perpendicular to the spectrometer wavelength dispersive axis at each wavelength to obtain the measured spectrum. The individual spectral shape at each wavelength is the point spread function (PSF) of the system at that specific wavelength.

When the measurement spot is imaged onto the detector such that the direction aligned with the plane of incidence on the wafer surface is oriented perpendicular to the direction of wavelength dispersion on the detector surface, the resulting point spread function (PSF) is much less dependent on wavelength compared to traditional configurations. The resulting PSF is less peaked because the image intensity does not vary greatly in the direction perpendicular to the elongated direction (e.g., across the short axis of the ellipse) for a given wavelength. Furthermore, although the image intensity does vary greatly in the elongation direction (e.g., across the long axis of the ellipse), the variations are integrated out since the elongation direction is aligned with the charge integration direction of the CCD. In this manner, the spectrometer does not have to acquire spectral data at high resolution to accurately construct the PSF. This reduces measurement time and increases throughput.

In another example, the resulting PSF for a particular wavelength is independent of the angle of incidence when the elongation direction is oriented perpendicular to the direction of spectral dispersion. The image, and corresponding intensity distribution perpendicular to the elongation direction (i.e., across the short axis of the ellipse) is largely invariant to angle of incidence. Thus, the image, and corresponding intensity distribution, projected in the direction of spectral dispersion is largely invariant to angle of incidence. Hence, the calculated PSFs show little dependence on the angle of incidence.

In another example, the resulting PSF is significantly less sensitive to focus errors compared to prior art configurations. As the measurement target on wafer moves in and out of focus, the detected image of the measurement spot on the wafer shifts location. Analogous to the description of FIG. 6, when wafer 120 is in focus, the beam of illumination light 117 illuminates the wafer at location A. The beam of collected light 127 is wavelength dispersed and imaged onto detector 141 over spots 142A and 142B as illustrated in FIG. 8. As the wafer 120 is moved upward in the z-direction and is defocused by an amount, $\Delta Z$, that is greater than zero, the beam of illumination light 117 illuminates the wafer at location C. The beam of collected light 127' is wavelength dispersed and imaged onto detector 141 over spots 142A' and 142B'. This shift in image location perpendicular to the wavelength dispersion direction minimizes spectral measurement errors induced by focus errors as the wavelength to pixel mapping remains unchanged. As the wafer 120 is moved downward in the z-direction and is defocused by an amount, $\Delta Z$, that is less than zero, the beam of illumination light 117 illuminates the wafer at location B. The beam of collected light 127" is wavelength dispersed and imaged onto detector 141 over spots 142A" and 142B". Again, this shift in image location perpendicular to the wavelength dispersion direction minimizes spectral measurement errors induced by focus errors.

In this configuration, focus errors shift the image on the detector in the direction perpendicular to the wavelength dispersion axis. Since the calculated spectrum is obtained by integrating the image perpendicular to spectrometer dispersive axis, the focus error induced image shift is integrated out and does not induce substantial spectral measurement error. This reduced sensitivity to focus errors eliminates the need to track and correct focus errors based on atomic line emission. In this manner, broadband light sources such as a high brightness Laser Driven Light Source (LDLS) may be employed as a light source in spectroscopic metrology systems such as system 100 with relaxed focus positioning requirements.

As described hereinbefore, the PSF projected by the spectrometer is largely determined by the distribution of light perpendicular to the plane of incidence (i.e., XZ plane). For this reason, the PSF is independent of the oblique angle of incidence. Thus, the dependence of the PSF on wavelength is substantially less than a traditional configuration.

As described herein any normal incidence or oblique incidence broadband optical metrology system may be configured such that the measurement spot is imaged onto the surface of the detector such that a direction aligned with the plane of incidence on the wafer surface is oriented perpendicular to a direction of wavelength dispersion on the detector surface. In some embodiments, the spectrometer dispersion axis is oriented orthogonal to wafer focus axis (e.g., z-axis in FIGS. 1-4) to further reduce the system sensitivity towards focus error.

In another aspect, the metrology systems described herein employ a multi-zone infrared detector that combines different sensitivity bands at different locations on a single detector package. The detector is configured to deliver a continuous spectrum of data at different sensitivities, depending on location of incidence.

Figure 10:
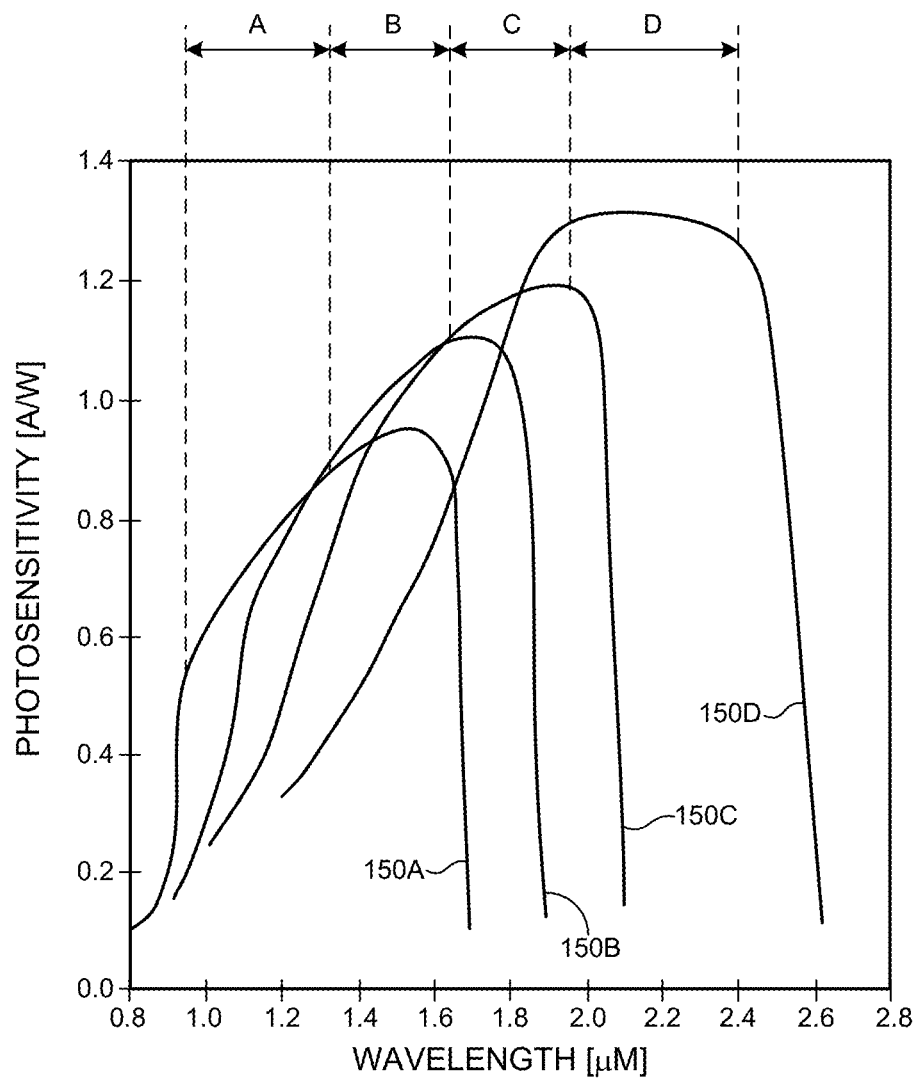
FIG. 10 illustrates typical photosensitivity curves of four available Indium Gallium Arsenide (InGaAs) sensors.

FIG. 10 illustrates typical photosensitivity curves of available Indium Gallium Arsenide (InGaAs) sensors. As depicted in FIG. 10, no single sensor of the available InGaAs sensors is capable of providing adequate photosensitivity across a wavelength band from 1 micrometer to 2.5 micrometers. Thus, individually, the available sensors are only capable of sensing over a narrow waveband. In some embodiments, each individual sensor is arranged in a cascaded arrangement, for example, as depicted in FIG. 4. However, this requires individual grating structures or combinations of beam splitting elements and grating structures to subdivide the collected light into each individual spectral range and disperse each spectral range onto each separate detector. This results in undesirable light loss and optical system complexity.

In one aspect, multiple sensor chips, each sensitive in a different waveband are combined into a single detector package. In turn, this multi-zone detector is implemented in the metrology systems described herein.

Figure 9:
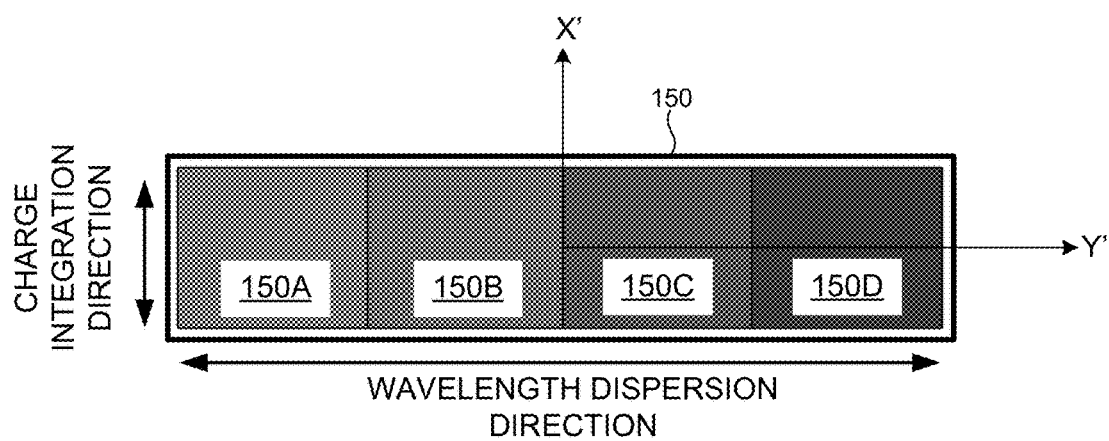
FIG. 9 depicts a normal view of the surface of detector 150 depicted in FIG. 1 in one embodiment.

FIG. 9 depicts four sensor chips 150A-D derived from four different wavebands to make a multi-zone infrared detector 150. As depicted in FIG. 10, the four sensor chips include different material compositions that each exhibit different photosensitivity characteristics. As depicted in FIG. 10, sensor chip 150A exhibits high sensitivity over a waveband, A, sensor chip 150B exhibits high sensitivity over a waveband, B, sensor chip 150C exhibits high sensitivity over a waveband, C, and sensor chip 150D exhibits high sensitivity over a waveband, D. A metrology system incorporating detector 150 is configured to disperse wavelengths within waveband A onto sensor chip 150A, disperse wavelengths within waveband B onto sensor chip 150B, disperse wavelengths within waveband C onto sensor chip 150C, and disperse wavelengths within waveband D onto sensor chip 150D. In this manner, high photosensitivity (i.e., high SNR) is achieved over the aggregate waveband that includes wavebands A-D from a single detector.

In some examples, a multi-zone detector includes InGaAs sensors with sensitivity to different spectral regions assembled in a single sensor package to produce a single, contiguous spectrum covering wavelengths from 750 nanometers to 3,000 nanometers, or beyond.

In general, any number of individual sensors may be assembled along the direction of wavelength dispersion of the multi-zone detector such that a contiguous spectrum maybe derived from the detector. However, typically, two to four individual sensors are employed in a multi-zone detector, such as detector 150.

In another further aspect, the dimension of illumination field stop projected on wafer plane in the direction perpendicular to the plane of incidence is adjusted to optimize the resulting measurement accuracy and speed based on the nature of target under measurement.

The illumination field stop projected on the wafer plane in the direction perpendicular to the plane of incidence is adjusted to shape the PSF to achieve a flat-top profile that is less sensitive to wavelength for each measurement application. In addition, the spectral resolution is adjusted to achieve optimize the measurement accuracy and speed based on the flat-top profile.

In some examples, e.g., if the sample is a very thick film or grating structure, the illumination field stop projected on wafer plane in the direction perpendicular to the plane of incidence is adjusted to reduce the field size to achieve increase spectral resolution. In some examples, e.g., if the sample is a thin film, the illumination field stop projected on wafer plane in the direction perpendicular to the plane of incidence is adjusted to increase the field size to achieve a shortened measurement time without losing spectral resolution.

In the embodiments depicted in FIGS. 1-4, computing system 130 is configured to receive signals 154 indicative of the spectral response detected by detectors 141, 150, and 153 (if applicable). Computing system 130 is further configured to determine control signals 119 that are communicated to programmable illumination field stop 113. Programmable illumination field stop 113 receives control signals 119 and adjusts the size of the illumination aperture to achieve the desired illumination field size.

In some examples, the illumination field stop is adjusted to optimize measurement accuracy and speed as described hereinbefore. In another example, the illumination field stop is adjusted to prevent image clipping by the spectrometer slit and corresponding degradation of measurement results. In this manner, the illumination field size is adjusted such that the image of the measurement target underfills the spectrometer slit. In one example, the illumination field stop is adjusted such that the projection of the polarizer slit of the illumination optics underfills the spectrometer slit of the metrology system.

Figure 11:
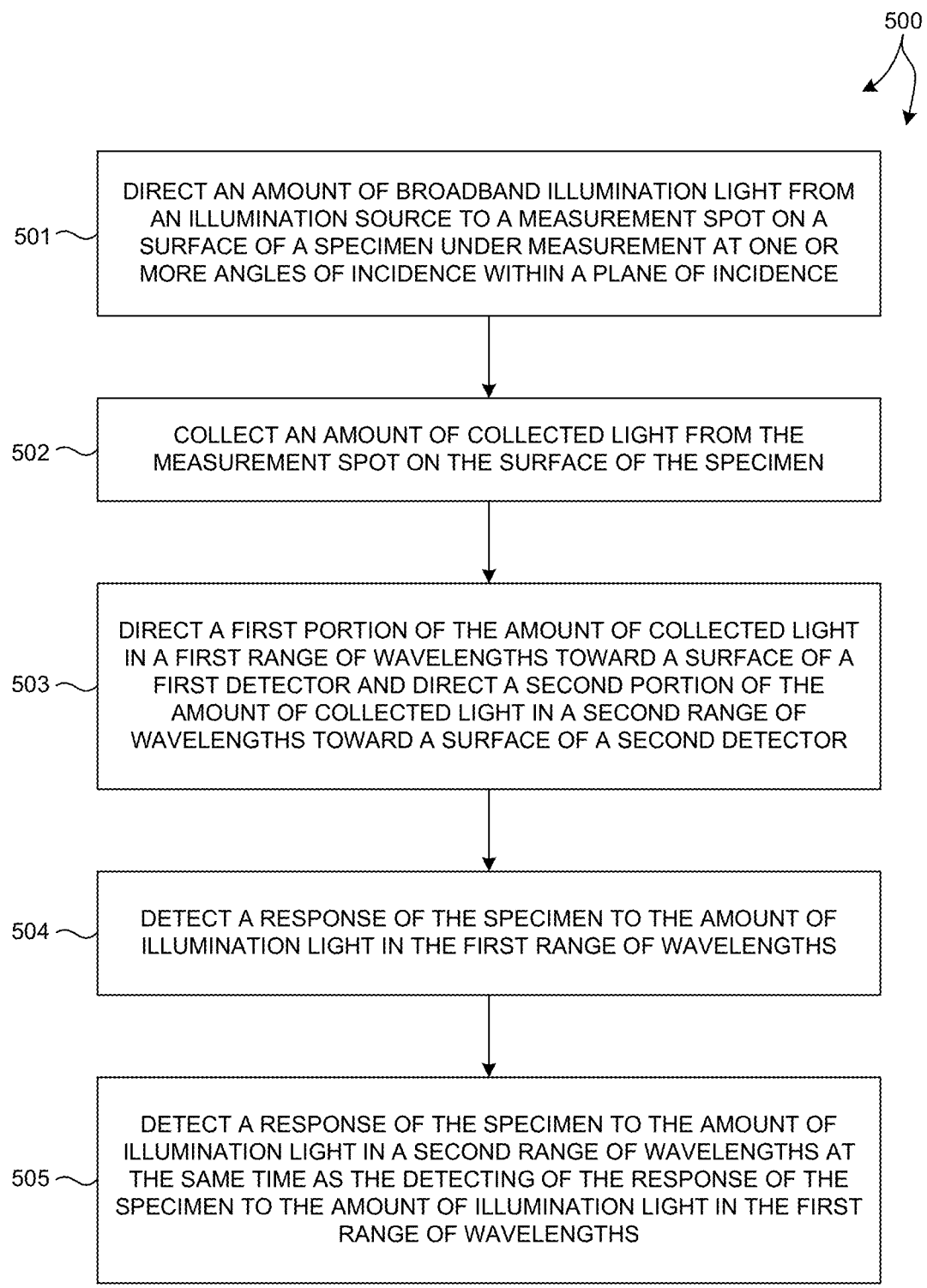
FIG. 11 illustrates a method 500 of performing simultaneous spectroscopic measurements of one or more structures at ultraviolet, visible, and infrared wavelengths in at least one novel aspect as described herein.

FIG. 11 illustrates a method 500 of performing spectroscopic measurements in at least one novel aspect. Method 500 is suitable for implementation by a metrology system such as metrology systems 100, 200, 300, and 400 illustrated in FIGS. 1-4 of the present invention, respectively. In one aspect, it is recognized that data processing blocks of method 500 may be carried out via a pre-programmed algorithm executed by one or more processors of computing system 130, or any other general purpose computing system. It is recognized herein that the particular structural aspects of metrology systems 100, 200, 300, and 400 do not represent limitations and should be interpreted as illustrative only.

In block 501, an amount of broadband illumination light from an illumination source is directed to a measurement spot on a surface of a specimen under measurement at one or more angles of incidence within a plane of incidence.

In block 502, an amount of light is collected from the measurement spot on the surface of the specimen.

In block 503, a first portion of the amount of collected light in a first range of wavelengths is directed toward a surface of a first detector and a second portion of the amount of collected light in a second range of wavelengths is directed toward a surface of a second detector.

In block 504, a response of the specimen to the amount of illumination light in the first range of wavelengths is detected.

In block 505, a response of the specimen to the amount of illumination light in the second range of wavelengths is detected at the same time the response of the specimen to the amount of illumination light in the first range of wavelengths is detected.

Exemplary measurement techniques that may be configured as described herein include, but are not limited to spectroscopic ellipsometry (SE), including Mueller matrix ellipsometry (MMSE), rotating polarizer SE (RPSE), rotating polarizer, rotating compensator SE (RPRC), rotating compensator, rotating compensator SE (RCRC), spectroscopic reflectometry (SR), including polarized SR, unpolarized SR, spectroscopic scatterometry, scatterometry overlay, beam profile reflectometry, both angle-resolved and polarization-resolved, beam profile ellipsometry, single or multiple discrete wavelength ellipsometry, etc. In general, any metrology technique that includes illumination having UV and IR wavelengths may be contemplated, individually, or in any combination. For example, any SR or SE technique applicable to the characterization of semiconductor structures, including image based metrology techniques, may be contemplated, individually, or in any combination.

In a further embodiment, systems 100, 200, 300, and 400 include one or more computing systems 130 employed to perform measurements of actual device structures based on spectroscopic measurement data collected in accordance with the methods described herein. The one or more computing systems 130 may be communicatively coupled to the spectrometer. In one aspect, the one or more computing systems 130 are configured to receive measurement data 154 associated with measurements of the structure of specimen 120.

It should be recognized that one or more steps described throughout the present disclosure may be carried out by a single computer system 130 or, alternatively, a multiple computer system 130. Moreover, different subsystems of systems 100, 200, 300, and 400, may include a computer system suitable for carrying out at least a portion of the steps described herein. Therefore, the aforementioned description should not be interpreted as a limitation on the present invention but merely an illustration.

In addition, the computer system 130 may be communicatively coupled to the spectrometers in any manner known in the art. For example, the one or more computing systems 130 may be coupled to computing systems associated with the spectrometers. In another example, the spectrometers may be controlled directly by a single computer system coupled to computer system 130.

The computer system 130 of the metrology systems 100, 200, 300, and 400 may be configured to receive and/or acquire data or information from the subsystems of the system (e.g., spectrometers and the like) by a transmission medium that may include wireline and/or wireless portions. In this manner, the transmission medium may serve as a data link between the computer system 130 and other subsystems of systems 100, 200, 300, and 400.

Computer system 130 of metrology systems 100, 200, 300, and 400 may be configured to receive and/or acquire data or information (e.g., measurement results, modeling inputs, modeling results, reference measurement results, etc.) from other systems by a transmission medium that may include wireline and/or wireless portions. In this manner, the transmission medium may serve as a data link between the computer system 130 and other systems (e.g., memory on-board metrology systems 100, 200, 300, and 400, external memory, or other external systems). For example, the computing system 130 may be configured to receive measurement data from a storage medium (i.e., memory 132 or an external memory) via a data link. For instance, spectral results obtained using the spectrometers described herein may be stored in a permanent or semi-permanent memory device (e.g., memory 132 or an external memory). In this regard, the spectral results may be imported from on-board memory or from an external memory system. Moreover, the computer system 130 may send data to other systems via a transmission medium. For instance, a measurement model or an estimated parameter value determined by computer system 130 may be communicated and stored in an external memory. In this regard, measurement results may be exported to another system.

Computing system 130 may include, but is not limited to, a personal computer system, mainframe computer system, workstation, image computer, parallel processor, or any other device known in the art. In general, the term "computing system" may be broadly defined to encompass any device having one or more processors, which execute instructions from a memory medium.

Program instructions 134 implementing methods such as those described herein may be transmitted over a transmission medium such as a wire, cable, or wireless transmission link. For example, as illustrated in FIG. 1, program instructions 134 stored in memory 132 are transmitted to processor 131 over bus 133. Program instructions 134 are stored in a computer readable medium (e.g., memory 132). Exemplary computer-readable media include read-only memory, a random access memory, a magnetic or optical disk, or a magnetic tape.

In some examples, the measurement models are implemented as an element of a SpectraShape® optical critical-dimension metrology system available from KLA-Tencor Corporation, Milpitas, Calif., USA. In this manner, the model is created and ready for use immediately after the spectra are collected by the system.

In some other examples, the measurement models are implemented off-line, for example, by a computing system implementing AcuShape® software available from KLA-Tencor Corporation, Milpitas, Calif., USA. The resulting, trained model may be incorporated as an element of an AcuShape® library that is accessible by a metrology system performing measurements.

Figure 12:
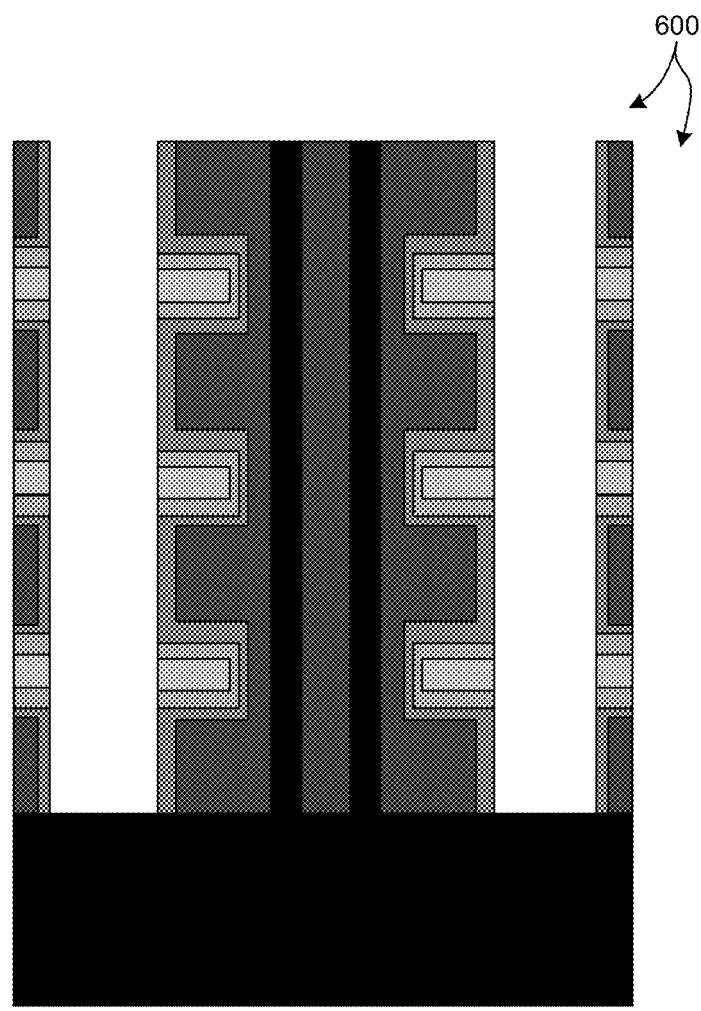
FIG. 12 depicts an exemplary high aspect ratio NAND structure 600 that suffers from low light penetration into the structure(s) being measured.

In another aspect, the methods and systems for spectroscopic metrology of semiconductor devices described herein are applied to the measurement of high aspect ratio (HAR) structures, large lateral dimension structures, or both. Exemplary structures suitable for measurement by the systems and methods described herein include three dimensional NAND structures, such as vertical-NAND (V-NAND) structures, dynamic random access memory structures (DRAM), etc., manufactured by various semiconductor manufacturers such as Samsung Inc. (South Korea), SK Hynix Inc. (South Korea), Toshiba Corporation (Japan), and Micron Technology, Inc. (United States), etc. These complex devices suffer from low light penetration into the structure(s) being measured. FIG. 12 depicts an exemplary high aspect ratio NAND structure 600 that suffers from low light penetration into the structure(s) being measured. A spectroscopic ellipsometer with broadband capability into the infrared, with simultaneous spectral band detection with multi-zone sensors as described herein is suitable for measurements of these high-aspect ratio structures.

In yet another aspect, the measurement results described herein can be used to provide active feedback to a process tool (e.g., lithography tool, etch tool, deposition tool, etc.). For example, values of measured parameters determined based on measurement methods described herein can be communicated to a lithography tool to adjust the lithography system to achieve a desired output. In a similar way etch parameters (e.g., etch time, diffusivity, etc.) or deposition parameters (e.g., time, concentration, etc.) may be included in a measurement model to provide active feedback to etch tools or deposition tools, respectively. In some example, corrections to process parameters determined based on measured device parameter values and a trained measurement model may be communicated to a lithography tool, etch tool, or deposition tool.

As described herein, the term "critical dimension" includes any critical dimension of a structure (e.g., bottom critical dimension, middle critical dimension, top critical dimension, sidewall angle, grating height, etc.), a critical dimension between any two or more structures (e.g., distance between two structures), and a displacement between two or more structures (e.g., overlay displacement between overlaying grating structures, etc.). Structures may include three dimensional structures, patterned structures, overlay structures, etc.

As described herein, the term "critical dimension application" or "critical dimension measurement application" includes any critical dimension measurement.

As described herein, the term "metrology system" includes any system employed at least in part to characterize a specimen in any aspect, including measurement applications such as critical dimension metrology, overlay metrology, focus/dosage metrology, and composition metrology. However, such terms of art do not limit the scope of the term "metrology system" as described herein. In addition, the metrology system 100 may be configured for measurement of patterned wafers and/or unpatterned wafers. The metrology system may be configured as a LED inspection tool, edge inspection tool, backside inspection tool, macro-inspection tool, or multi-mode inspection tool (involving data from one or more platforms simultaneously), and any other metrology or inspection tool that benefits from the calibration of system parameters based on critical dimension data.

Various embodiments are described herein for a semiconductor measurement system that may be used for measuring a specimen within any semiconductor processing tool (e.g., an inspection system or a lithography system). The term "specimen" is used herein to refer to a wafer, a reticle, or any other sample that may be processed (e.g., printed or inspected for defects) by means known in the art.

As used herein, the term "wafer" generally refers to substrates formed of a semiconductor or non-semiconductor material. Examples include, but are not limited to, monocrystalline silicon, gallium arsenide, and indium phosphide. Such substrates may be commonly found and/or processed in semiconductor fabrication facilities. In some cases, a wafer may include only the substrate (i.e., bare wafer). Alternatively, a wafer may include one or more layers of different materials formed upon a substrate. One or more layers formed on a wafer may be "patterned" or "unpatterned." For example, a wafer may include a plurality of dies having repeatable pattern features.

A "reticle" may be a reticle at any stage of a reticle fabrication process, or a completed reticle that may or may not be released for use in a semiconductor fabrication facility. A reticle, or a "mask," is generally defined as a substantially transparent substrate having substantially opaque regions formed thereon and configured in a pattern. The substrate may include, for example, a glass material such as amorphous $SiO_2$. A reticle may be disposed above a resist-covered wafer during an exposure step of a lithography process such that the pattern on the reticle may be transferred to the resist.

One or more layers formed on a wafer may be patterned or unpatterned. For example, a wafer may include a plurality of dies, each having repeatable pattern features. Formation and processing of such layers of material may ultimately result in completed devices. Many different types of devices may be formed on a wafer, and the term wafer as used herein is intended to encompass a wafer on which any type of device known in the art is being fabricated.

In one or more exemplary embodiments, the functions described may be implemented in hardware, software, firmware, or any combination thereof. If implemented in software, the functions may be stored on or transmitted over as one or more instructions or code on a computer-readable medium. Computer-readable media includes both computer storage media and communication media including any medium that facilitates transfer of a computer program from one place to another. A storage media may be any available media that can be accessed by a general purpose or special purpose computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code means in the form of instructions or data structures and that can be accessed by a general-purpose or special-purpose computer, or a general-purpose or special-purpose processor. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, includes compact disc (CD), laser disc, optical disc, digital versatile disc (DVD), floppy disk and blu-ray disc where disks usually reproduce data magnetically, while discs reproduce data optically with lasers. Combinations of the above should also be included within the scope of computer-readable media.

Although certain specific embodiments are described above for instructional purposes, the teachings of this patent document have general applicability and are not limited to the specific embodiments described above. Accordingly, various modifications, adaptations, and combinations of various features of the described embodiments can be practiced without departing from the scope of the invention as set forth in the claims.

What is claimed is:

1. A metrology system comprising:
one or more illumination sources configured to generate an amount of broadband illumination light;

an illumination optics subsystem configured to direct the amount of illumination light from the illumination source to a measurement spot on a surface of a specimen under measurement at one or more angles of incidence within a plane of incidence;

a collection optics subsystem configured to collect an amount of collected light from the measurement spot on the surface of the specimen;

a first detector having a planar, two-dimensional surface sensitive to incident light, wherein the first detector is configured to detect a response of the specimen to the amount of illumination light in a first range of wavelengths;

a second detector having a planar, two-dimensional surface sensitive to incident light, wherein the second detector is configured to detect a response of the specimen to the amount of illumination light in a second range of wavelengths at the same time the first detector detects the response of the specimen to the amount of illumination light in the first range of wavelengths by the first detector;

a first diffractive element configured to disperse a first portion of the amount of collected light in the first range of wavelengths toward the surface of the first detector and reflect or transmit a second portion of the amount of collected light in the second range of wavelengths into a zero diffraction order; and a second diffractive element configured to disperse the second portion of the amount of collected light in the second range of wavelengths toward the surface of the second detector.

2. The metrology system of claim 1, wherein the collection optics subsystem images the measurement spot onto the surface of the first detector such that a direction aligned with the plane of incidence projected on the first detector is oriented perpendicular to a direction of wavelength dispersion on the surface of the first detector.

3. The metrology system of claim 2, wherein the collection optics subsystem images the measurement spot onto the surface of the second detector such that a direction aligned with the plane of incidence projected on the second detector is oriented perpendicular to a direction of wavelength dispersion on the surface of the second detector.

4. The metrology system of claim 1, wherein the second detector includes two or more different surface areas each having different photosensitivity, wherein the two or more different surface areas are aligned with a direction of wavelength dispersion across the surface of the second detector.

5. The metrology system of claim 1, further comprising:
a third detector having a planar, two-dimensional surface sensitive to incident light, wherein the third detector is configured to detect a response of the specimen to the amount of illumination light in a third range of wavelengths at the same time the first detector detects the response of the specimen to the amount of illumination light in the first range of wavelengths; and
a third diffractive element configured to disperse a third portion of the amount of collected light in the third range of wavelengths toward the surface of the third detector.

6. The metrology system of claim 1, further comprising:
a fine focus sensor configured to detect a portion of the amount of collected light; and
a beamsplitting element configured to direct the portion of the amount of collected light to the fine focus sensor, wherein the fine focus sensor is configured to detect specimen focus error at the same time the first and second detectors detect the response of the specimen to the amount of illumination light.

7. The metrology system of claim 1, wherein the amount of illumination light is broadband illumination light includes a range of wavelengths including infrared, visible, and ultraviolet wavelengths.

8. The metrology system of claim 1, wherein at least a portion of the amount of illumination light is provided to the specimen at a normal angle of incidence.

9. The metrology system of claim 1, wherein at least a portion of the amount of illumination light is provided to the specimen at an oblique angle of incidence.

10. The metrology system of claim 1, wherein the metrology system is configured as any one or more of a spectroscopic ellipsometer and a spectroscopic reflectometer.

11. The metrology system of claim 1, wherein the specimen under measurement is a high aspect ratio metrology target.

12. The metrology system of claim 1, wherein the specimen under measurement is a three dimensional NAND structure or a dynamic random access memory structure.

13. The metrology system of claim 1, further comprising:
a computing system configured to generate an estimated value of a parameter of interest of the specimen under measurement based on a combined analysis of the output of first and second detectors.

14. A metrology system comprising: one or more illumination sources configured to generate an amount of broadband illumination light; an illumination optics subsystem configured to direct the amount of illumination light from the illumination source to a measurement spot on a surface of a specimen under measurement at one or more angles of incidence within a plane of incidence; a collection optics subsystem configured to collect an amount of collected light from the measurement spot on the surface of the specimen; a first detector having a planar, two-dimensional surface sensitive to incident light, wherein the first detector is configured to detect a response of the specimen to the amount of illumination light in a first range of wavelengths, wherein the first detector includes two or more different surface areas each having different photosensitivity, wherein the two or more different surface areas are aligned with a direction of wavelength dispersion across the surface of the first detector, wherein the collection optics subsystem images the measurement spot onto the surface of the first detector such that a direction aligned with the plane of incidence projected on the first detector is oriented perpendicular to the direction of wavelength dispersion across the surface of the first detector; and a first diffractive element configured to disperse a first portion of the amount of collected light in the first range of wavelengths across the surface of the first detector.

15. The metrology system of claim 14, further comprising:
a second detector having a planar, two-dimensional surface sensitive to incident light, wherein the second detector is configured to detect a response of the specimen to the amount of illumination light in a second range of wavelengths at the same time the first detector detects the response of the specimen to the amount of illumination light in the first range of wavelengths; and
a second diffractive element configured to disperse a second portion of the amount of collected light in the second range of wavelengths across the surface of the second detector.

16. The metrology system of claim 14, further comprising:
a third detector having a planar, two-dimensional surface sensitive to incident light, wherein the third detector is configured to detect a response of the specimen to the amount of illumination light in a third range of wavelengths at the same time the first detector detects the response of the specimen to the amount of illumination light in the first range of wavelengths; and
a third diffractive element configured to disperse a third portion of the amount of collected light in the third range of wavelengths across the surface of the third detector.

17. The metrology system of claim 14, further comprising:
a fine focus sensor configured to detect a portion of the amount of collected light; and
a beamsplitting element configured to direct the portion of the amount of collected light to the fine focus sensor.

18. The metrology system of claim 14, wherein the specimen under measurement is a three dimensional NAND structure or a dynamic random access memory structure.

19. A method comprising:
directing an amount of broadband illumination light from an illumination source to a measurement spot on a surface of a specimen under measurement at one or more angles of incidence within a plane of incidence;
collecting an amount of collected light from the measurement spot on the surface of the specimen;
directing a first portion of the amount of collected light in a first range of wavelengths toward a surface of a first detector and directing a second portion of the amount of collected light in a second range of wavelengths toward a surface of a second detector;
imaging the measurement spot onto the surface of the first detector such that a direction aligned with the plane of incidence projected on the first detector is oriented perpendicular to a direction of wavelength dispersion on the surface of the first detector;
detecting a response of the specimen to the amount of illumination light in the first range of wavelengths; and
detecting a response of the specimen to the amount of illumination light in the second range of wavelengths at the same time as the detecting of the response of the specimen to the amount of illumination light in the first range of wavelengths.

20. The method of claim 19, wherein the second detector includes two or more different surface areas each having different photosensitivity, wherein the two or more different surface areas are aligned with a direction of wavelength dispersion across the surface of the second detector.

21. The method of claim 19, further comprising:
directing a third portion of the amount of collected light in a third range of wavelengths toward a surface of a third detector; and
detecting a response of the specimen to the amount of illumination light in the third range of wavelengths at the same time as the detecting of the response of the specimen to the amount of illumination light in the first range of wavelengths.

22. The method of claim 19, wherein the specimen under measurement is a three dimensional NAND structure or a dynamic random access memory structure.

* * * * *